US011549098B2

(12) United States Patent
James

(10) Patent No.: US 11,549,098 B2
(45) Date of Patent: Jan. 10, 2023

(54) PROCESSING OF SPERM CELLS

(71) Applicant: Fertility Innovations Limited, Dorchester (GB)

(72) Inventor: Michael Howard James, Dorset (GB)

(73) Assignee: FERTILITY INNOVATIONS LIMITED, Dorset (GB)

( * ) Notice: Subject to any disclaimer, the term of this patent is extended or adjusted under 35 U.S.C. 154(b) by 734 days.

(21) Appl. No.: 14/384,277

(22) PCT Filed: Mar. 15, 2013

(86) PCT No.: PCT/GB2013/050668
§ 371 (c)(1),
(2) Date: Sep. 10, 2014

(87) PCT Pub. No.: WO2013/136091
PCT Pub. Date: Sep. 19, 2013

(65) Prior Publication Data
US 2015/0037864 A1   Feb. 5, 2015

(30) Foreign Application Priority Data

Mar. 16, 2012 (GB) .................................. 1204722
Mar. 19, 2012 (GB) .................................. 1204819

(51) Int. Cl.
*C12N 5/076* (2010.01)
*C12N 13/00* (2006.01)

(52) U.S. Cl.
CPC ............. *C12N 5/061* (2013.01); *C12N 13/00* (2013.01)

(58) Field of Classification Search
None
See application file for complete search history.

(56) References Cited

U.S. PATENT DOCUMENTS

| 5,039,386 | A | 8/1991 | Margolis | |
|---|---|---|---|---|
| 5,650,055 | A | 7/1997 | Margolis | |
| 5,686,302 | A | 11/1997 | Zech | |
| 2001/0052462 | A1* | 12/2001 | Ogle | B01D 61/425 204/518 |
| 2005/0026274 | A1 | 2/2005 | Zech | |
| 2006/0144707 | A1 | 7/2006 | Landers et al. | |
| 2009/0101507 | A1* | 4/2009 | Aitken | B01D 71/50 204/540 |
| 2009/0134031 | A1* | 5/2009 | Ogle | B01D 57/02 204/606 |

FOREIGN PATENT DOCUMENTS

| AU | 738361 B2 | 9/2001 |
|---|---|---|
| GB | 2360360 A | 9/2001 |
| WO | WO-2001/078878 A1 | 10/2001 |
| WO | WO-2002/004314 A1 | 1/2002 |
| WO | WO-2002/024314 A1 | 3/2002 |
| WO | WO-2002/093168 A1 | 11/2002 |
| WO | WO-2004/046712 A2 | 6/2004 |
| WO | WO-2004/053465 A2 | 6/2004 |
| WO | WO-2005/033295 A1 | 4/2005 |
| WO | WO-2012/032165 A1 | 3/2012 |
| WO | WO-2013/186567 A1 | 12/2013 |

OTHER PUBLICATIONS

Vasudevan, Treatment of sperm with extracellular adenosine 5'-triphosphate improves the in vitro fertility rate of inbred and enetically modified mice with low fertility, Theriogenology. Sep. 1, 2011; 76(4): 729-736.*
Roudebush et al., Platelet-activating factor significantly enhances intrauterine insemination pregnancy rates in non-male factor infertility, Fertility and Sterility, vol. 82, No. 1, Jul. 2004.*
Aitken et al., Paradoxical stimulation of human sperm motility by 2-deoxyadenosine, Journal Reproduction Fertility, 1986, vol. 78, pp. 515-527.*
Phospholipids, Webpage 2016.*
Phospholipids, Defining characteristics of Phospholipids, Boundless. com WebEntry, 2017.*
Krishnamurthy, Role of pKa of Nucleobases in the Origins of Chemical Evolution, Accounts of Chemical Research, vol. 45 , No. 12, p. 2035-2044, 2012.*
Goh et al., Constant pH Molecular Dynamics Simulations of Nucleic Acidsin Explicit Solvent, Chem Theory Comput. Jan. 10, 2012; 8(1): 36-46.*
Al-Ghobashy et al., Electrophoretic behavior of charge regulated zwitterionic buffers in covalently and dynamically coated fused silica capillaries, Bulletin of Faculty of Pharmacy, Cairo University (2014) 52, 71-78 (Year: 2014).*
Lumen, The effect of pH onSolubility, Webpage, 2020 (Year: 2020).*
Duran et al., Sperm DNA quality predicts intrauterine insemination outcome: a prospective cohort study, Human Reproduction vol. 17, No. 12 pp. 3122-3128, 2002 (Year: 2002).*
Fields et al., Purification and Immunohistochemical Localization of Relaxin in the Human Term Placenta, The Journal of Clinical Endocrinology & Metabolism, vol. 52, Issue 1, 1981 (Year: 1981).*
Lewis , Acids and Bases—The Lewis Definition, Webpage, 2021 (Year: 2021).*
Will et al., Biological pH buffers in IVF: help or hindrance to success, J. Assist Reprod. Genet., 2011, 28:711-724 (Year: 2011).*
Bani et al., Relaxin: A pleiotropic Hormone, General Pharmac. Vol. 28, No. 1, 13-22, 1997 (Year: 1997).*
Fleming, Steven, and R. John Aitken. "Electrophoretic sperm separation." Sperm Chromatin. Springer, New York, NY, 2011. 423-429. (Year: 2011).*
Ainsworth, C., et al. (2005) "Development of a novel electrophoretic system for the isolation of human spermatozoa", *Human Reproduction*, 20(8):2261-2270.

(Continued)

*Primary Examiner* — Robert J Yamasaki
(74) *Attorney, Agent, or Firm* — Harness Dickey & Pierce P.L.C.

(57) ABSTRACT

A process for separating sperm cells from a chemical compound by electrophoresis comprising subjecting the sperm cells to an electric potential between a cathode and an anode such that the sperm cells are separated from the chemical compound, and related methods including methods of using said sperm cells in intrauterine insemination.

9 Claims, 3 Drawing Sheets

(56) References Cited

OTHER PUBLICATIONS

Ainsworth, C., et al. (2006) "Development of a novel electrophoretic system for the isolation of human spermatozoa", *Journal of Urology*, 175(2):662-663—Editorial Comments by Craig Niederberger, M.D. Only.
Aitken, R.J., et al. (2011) "Electrophoretic sperm isolation: optimization of electrophoresis conditions and impact on oxidative stress", *Human Reproduction*, 26(8):1955-1964.
International Search Report and Written Opinion dated Sep. 6, 2013 issued in PCT Application No. PCT/GB2013/051556.
International Preliminary Report on Patentability and Written Opinion dated Sep. 16, 2014 issued in PCT Application No. PCT/GB2013/050668.
Search Report dated Oct. 10, 2012 issued in GB Application No. GB1210496.4.
Search Report dated Jul. 3, 2012 issued in GB Application No. GB1204722.1.
Ainsworth, C., et al. (2007), "First recorded pregnancy and normal birth after ICSI using electrophoretically isolated spermatozoa", *Human Reproduction*, 22(1): 197-200.
Fleming, S.D., et al. (2008) "Prospective controlled trial of an electrophoretic method of sperm preparation for assisted reproduction: comparison with density gradient centrifugation", *Human Reproduction*, 23(12): 2646-2651.
International Search Report dated Jul. 4, 2013 issued in PCT/GB2013/050668.
U.S. Appl. No. 14/406,577, filed Dec. 9, 2014.
Office Action dated Jan. 11, 2017 issued in U.S. Appl. No. 14/406,577.
Perumal P. (2008) "Cryopreservation of Bovine Semen with some Additives for Augmenting Fertility" Journal of Veterinary Research.
Hammitt, D. G. et al., (1989) "Comparison of Motility Stimulatns for Cryopreserved Human Semen" Fertility and Sterility, 52:3, 495-502.
Office Action dated Nov. 2, 2017 Issued in U.S. Appl. No. 14/406,577.
Wang, P., et al., "Study on the effect of cryoprotectant and sperm activator on sperm function after freezing and rewarming," Chinese Journal of Andrology, 10(4): 213-216 (1996).

\* cited by examiner

PROCESSING OF SPERM CELLS

PRIORITY STATEMENT

This application is a national stage application under 35 U.S.C. § 371 of PCT International Application No. PCT/GB2013/050668, which has an International filing date of 15 Mar. 2013 and claims priority to GB Application No. 1204722.1 filed on 16 Mar. 2012 and GB Application No. 1204819.5 filed on 19 Mar. 2012. The contents of each application recited above are incorporated herein by reference in their entirety.

BACKGROUND

It is estimated that 1 in 7 human couples have problems conceiving. Estimates put the percentage of cases of infertility that can be ascribed to the male partner at between 25% and 50%, depending on the population. The principal cause of male infertility is poor semen quality. Poor semen quality can be caused by a reduced number of spermatozoa ("sperm cells") and/or reduced motility (asthenozoospermia) of those cells that are present. A number of treatments are available for both male and female infertility including intracervical insemination (ICI) and intrauterine insemination (IUI). In essence, these procedures involve placing either recently collected sperm or sperm which has been frozen and thawed into the cervix, typically after washing, into the uterus by artificial means. IUI has great potential to be used in many cases of infertility currently treated by in vitro fertilisation (IVF). However, IUI typically suffers from low success rates primarily attributed to low semen quality.

Such techniques are also important in veterinary medicine including livestock breeding and conservation biology, where poor animal fertility may be a barrier to commercial or conservation goals. The chances of IUI treatment resulting in a pregnancy is greatly increased if the sperm cells used can be of the highest possible quality. Quality may be improved by any or all of the following:

- pre "washing" of sperm, for example in Hams F-10 media without L-glutamine, to remove seminal fluid, leukocytes and non-motile sperm;
- separation techniques to enrich the sample with higher quality cells, for example by discontinuous gradient configuration or electrophoresis (see, for example, WO2005/033295);
- treatment of the cells ex-vivo with a chemical agent in order to increase motility or otherwise improve their fertilisation capability.

Pre-treatment of cells with a chemical agent to improve fertilisation capability is usually followed by a washing step both in order to prevent exposure of the female partner, zygote and embryo to the chemical agent and to prevent "burn out" of the sperm cells which may result if their motility is stimulated for too-prolonged a period of time such that when insemination takes place the sperm cells are "exhausted" or have undergone premature triggering of the acrosome reaction.

Common to all pre-treatment procedures is the imperative that the procedure be as fast as possible (because sperm quality decreases with time ex-vivo) and that it avoids as far as possible physical and chemical trauma (for example shearing forces) which may damage cells.

Professor John Aitken and colleagues have developed an electrophoretic system (therein referred to as the "Aitken process" or "Aitken technique") for the isolation of human spermatozoa (see Ainsworth et al. 2005, Hum. Repro. 20(8) 2261-2270; and Aitken et al. 2011. Hum. Repro. 26(8) 1955-1964) which results in a sample for use in insemination comprising cells with less DNA damage than conventional density gradient centrifugation technologies of cell preparation. In essence, the technique of Aitken involves use of a separation cassette comprising two buffer-filled chambers separated by a membrane permeable to ions and sperm cells. A sample of semen is placed in one chamber and an electric field placed across the cassette. Within seconds sperm cells migrate in the electric field through the membrane to the second chamber. The small size of sperm cells makes them especially mobile in an electric field and the sialic acid on the cell surface causes migration to the positive electrode. Contaminating cells, for example, leukocytes and damaged and/or dead and or improperly matured cells, are much less mobile and thus the cell sample can be enriched for high quality sperm cells of use in subsequent fertility treatments.

The present invention is based on an adaptation of the Aitken technique to removal of chemical agents from sperm cells by electrophoresis either as a stand-alone technique or, advantageously, for use in combination with the Aitken technique whereby cells are enriched for high quality cells simultaneously to being washed of pre-treatment chemical agents. As such the invention is especially suitable for use in methods involving ex vivo treatment of sperm cells with a chemical compound to increase their fertilisation capability followed by the removal of the treatment chemical compound.

SUMMARY OF INVENTION

The invention provides in a first aspect, a process for separating sperm cells from a chemical compound by electrophoresis comprising subjecting the sperm cells to an electric potential between a cathode and an anode such that the sperm cells are separated from the chemical compound.

The invention also provides use of a sperm cell separated from a chemical compound by electrophoresis according to a process of the first aspect of invention in intrauterine insemination (IUI), in vitro fertilisation (IVF) or intracytoplasmic sperm injection (ICSI).

The invention also provides a method of treating sperm cells with a chemical compound in order to increase the sperm cell's fertilisation ability, comprising contacting the sperm cells with a chemical compound and then separating the sperm cells from the chemical compound by electrophoresis comprising subjecting the sperm cells to an electrical potential between a cathode and an anode such that the sperm cells are separated from the chemical compound.

DETAILED DESCRIPTION

Figure 1:
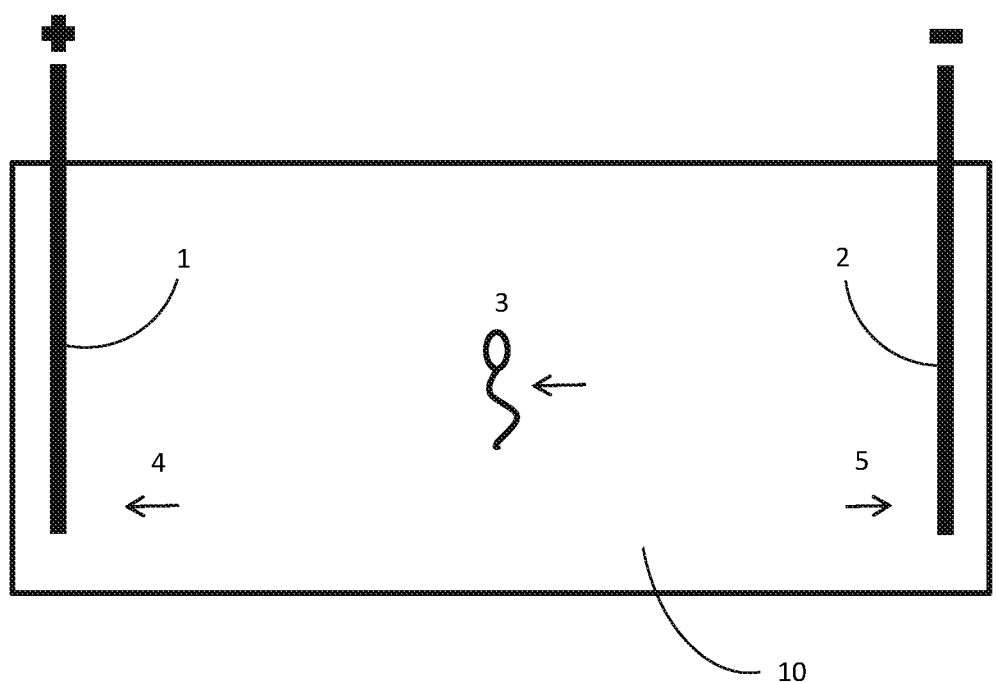
FIG. 1 is a diagram illustrating the principle of electrophoretic mobility of sperm cells and charged chemical compounds.

The invention provides a process for separating sperm cells from a chemical compound by electrophoresis comprising subjecting the sperm cells to an electric potential between a cathode and anode such that the sperm cells are separated from the chemical compound.

Sperm Cells

The sperm cells for use in the invention will typically have been collected from a male animal (for example a human subject) by any suitable method including masturbation, prostate massage, the use of an artificial vagina (for example as part of a breeding mount used for collection from male horses, cattle or other non-human animals), vibroejaculation and electroejaculation. Under some circumstances collection may involve use of a collection condom or retrieval directly from testes by testicular sperm extraction (TESE). Collection involving ejaculation is generally favoured because it will result in a sample of sperm cells suspended in semen and therefore more likely to be properly matured. The sperm cells may be collected "fresh" or may have been collected previously and frozen for a period of storage and then thawed when required for use. They may optionally be subjected to a pre-treatment step before use in a process or method of the invention.

Source of Sperm Cells

The various aspects of the invention primarily relate to humans. However, they may be applicable to other animals (especially other mammals) including livestock (especially horses, cattle, pigs), racing animals (especially horses and camels), companion animals (including cats and dogs), wild animals (including big cats, antelopes and pandas) and research animals (including rodents such as rabbits, mice and rats).

Chemical Compounds

The chemical compound(s) will typically be compounds to which the cells have been exposed ex-vivo in order to assist in freezing, or to improve sperm cell quality, for example, motility promoting agents, or to otherwise nourish, protect or otherwise enhance the cell's function, survival or health. It will usually be advantageous to remove the compounds from the cells before the cells are used for insemination. The cells may have been exposed to more than one compound and the compound(s) will typically have an electrical charge in solution (under physiologically suitable conditions) which may be positive or negative such that the compound(s) will exhibit electrophoretic migration when exposed to an electrical potential. Compounds may have an inherent electrical charge (for example they may be acids or bases) or a charge may have been introduced by derivatising the molecule with a charged moiety. Preferably, the chemical compounds are of sufficiently low molecular weight (for example, less than 50, 20 or 10 kDa) to allow their electrophoretic passage via through a size exclusion membrane having a pore size sufficient to exclude the electrophoretic passage of sperm cells (for example human sperm cells).

Electrophoretic Mobility of Sperm Cells

Healthy and properly-matured sperm cells express sialic acid residues on their surface which gives them a negative surface charge and allows them to migrate electrophoretically when subjected to an electrical potential. Sperm cells are especially suitable for techniques using electrophoretic mobility both because of their surface charge and because of their relatively small size which means that they are typically more rapidly mobile in an electric field than larger cell types. Their relatively small size also allows them to pass through membranes having a pore size which may retain other large cell types. The rapidity with which sperm cells migrate in response to an electric potential is advantageous because it allows electrophoretic techniques involving movement of sperm cells in response to an electric field to be quick and therefore likely to have minimal impact on cell viability.

Simple Separation of Cells from Chemical Compound(s)

In its most basic form the invention involves exposing a mixture of sperm cells and chemical compounds to an electric potential which causes the chemical compounds to migrate towards a higher or lower electrical potential depending on whether the chemical compounds carry a positive or negative charge.

For example, referring to FIG. 1:

A chamber (10) having an anode (1) and a cathode (2) across which a voltage is applied and containing an ionic solution may be provided, for example a physiological medium. Sperm cells (3) expressing surface sialic acid will migrate toward the anode. Chemical compounds having a negative charge (4) will migrate towards the anode and chemical compounds having a positive charge (5) will migrate towards the cathode.

Figure 2:
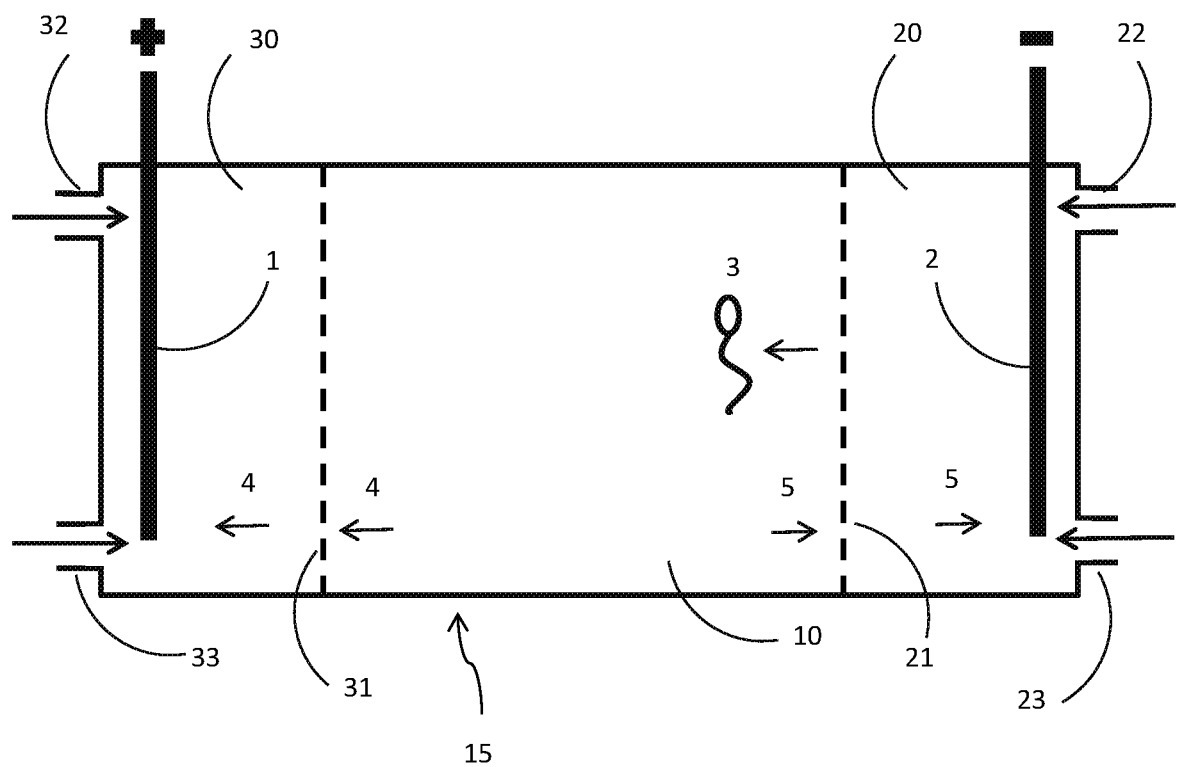
FIG. 2 is a diagram illustrating the use of ion permeable and chemical compound permeable membranes in order to separate sperm cells from chemical compounds in accordance with the invention.

In practice, the chamber (10) is preferably provided as part of a cassette (25) comprising of multiple chambers, for example the cassette (15) illustrated in FIG. 2:

The sample of sperm cells is introduced into sample input chamber (10) and the cells migrate under the influence of the electric potential as illustrated by reference to FIG. 1. The cathode (2) and anode (1) are provided in separate electrolyte-filled chambers (30) and (20) which are in ionic and therefore electrical communication with sample input chamber (10). Chambers (30) and (10) and (10) and (20) are separated by ion-permeable membranes (31, 21) which are impermeable to sperm cells. The provision of anodic chamber (30) and cathodic chamber (20) has the advantage that the cells are kept away from the electrodes and also that fresh electrolyte may be bathed over the electrodes by means of input and output ports (32, 33 and 22, 23). As such the electrolyte supply to the electrode chambers may be arranged as described in WO 01/78878, incorporated herein by reference.

If membrane (31) is made permeable to negatively charged chemical compounds (4) but not to sperm cells (3), it can be seen that negatively charged compounds (4) will migrate from chamber (10) to chamber (30) and be separated from cells (3) which are retained in chamber (10).

If membrane (21) is made permeable to positively charged chemical compound (5) but not to sperm cells, it can be seen that positively charged compound (5) will migrate from chamber (10) to chamber (20) and be separated from cells (3) which are retained in chamber (10).

As illustrated in FIG. 2 and described herein, cathodic chamber (20) contains a cathode and anodic chamber (30) contains an anode. However, also within the scope of all embodiments of the invention are arrangements wherein one or more of the respective electrodes is provided at a location (for example, further chambers) in electrical (for example ionic) communication with the respective cathodic and anodic chambers. All that is required is that the cathodic chamber (20) is at a lower (more negative) electrical potential than the sample input chamber (10) and that the anodic chamber (30) is at a higher (more positive) electrical potential than the sample input chamber (10).

Separation Membranes

Further instruction on the application of separation membranes to electrophoresis may be found in U.S. Pat. Nos. 5,039,386, 5,650,055, AU 738361 and WO 02/24314, all incorporated herein by reference.

Optionally the cassette (15) includes means of circulating electrolyte from an electrolyte reservoir(s) through the respective electrode chambers (20, 30). The ion permeable membrane and in fact all membranes for use with the present invention preferably prevents substantial convective mixing of the content of the adjacent chambers.

The membranes may be as described in WO 2005/033295, hereby incorporated by reference.

Solutions

In accordance with the processes of the invention, the chambers are filled with ionic buffers ("electrolytes") in use.

Preferred buffer concentrations are between about 1 to 100 mM. Any suitable buffer or electrolyte can be used. Suitable buffers include, but not limited to, sperm-compatible biological buffers and components such as HEPPS, HEPES, BisTris, sodium chloride, phosphate buffer salts, sucrose, glucose and mannitol. As outlined below, a 10 mM buffer of HEPES, 30 mM NaCl and 0.2 M sucrose has been found to be particularly useful. It will be appreciated, however, that any other suitable buffer can be used. Suitable buffers for use with mammalian sperm must be "non-capacitating", in that they do not cause premature capacitation of the sperm cells.

Integration of Processes with Sperm Cell Enrichment Techniques

As a minimum, the processes of the invention relate to separation of sperm cells from chemical compounds by electrophoresis. However, it will be appreciated that processes of the invention are especially suitable for integration into the "Aitken method" of sperm cell enrichment as described in WO 2005/033295.

The Aitken method is based on the realisation that higher quality sperm cells carry more sialic acid on their surface and are therefore capable of exhibiting greater electrophoretic mobility under the influence of an electrical potential. Without wishing to be bound by theory this is thought to be because a strong level of cell-surface sialic acid expression is a marker for proper sperm cell maturation.

Figure 3:
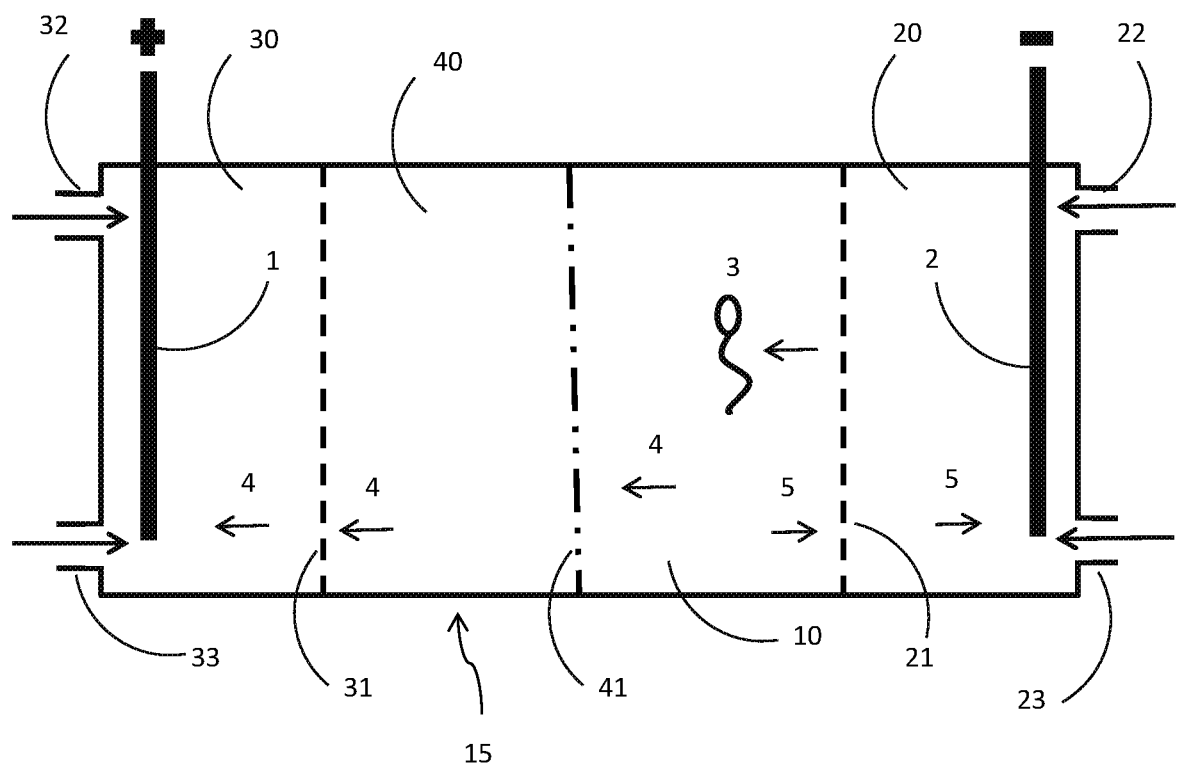
FIG. 3 is a diagram illustrating the use of the process of the invention in conjunction with the Aitken method of enriching sperm cells for quality.

A separation cassette suitable for an integrated process wherein a sperm cell sample is both enriched for high quality sperm cells and "washed" of chemical compounds is illustrated in FIG. 3:

Chambers (20, 30), electrodes (1 and 2), membranes (31, 21) electrolyte handling apparatus (32, 33, 22, 23) may be as described above with reference to FIG. 2. Disposed between anodic chamber (30) and cathodic chamber (20) are both sample input chamber (10) and sample output chamber (40). These chambers are separated by membrane (41) which is permeable to ions (and hence an electrical current) and permeable to the chemical compounds (4, 5) and also to sperm cells. Preferably, membrane (41) does not permit the electrophoretic passage of cells larger than sperm cells (for example leukocytes) nor does it permit substantial convective mixing between chambers (10) and (40). Further details of suitable membrane may be found in WO 05/033295, incorporated herein by reference.

The apparatus of FIG. 3 is preferably used by placing a sample of sperm cells in the sample input chamber (10). An electrical potential results in healthy sperm cells migrating through membrane (41) to sample output chamber (40) where they may be withdrawn for use. Less healthy sperm cells exhibit less electrophoretic mobility and are therefore more likely to remain in sample input chamber (10).

Chemical compounds having a positive charge (5) will migrate in an opposite direction to the sperm cells and will therefore remain in chamber (10) or migrate through membrane (21) to cathodic chamber (20) thereby being separated from healthy sperm cells in sample output chamber (40).

Chemical compounds having a negative charge (4) will migrate in the same direction as healthy sperm cells and will therefore pass from sample input chamber (10) to sample output chamber (40). They may then be separated from healthy sperm cells by virtue of membrane (31) being permeable to chemical compounds but not sperm cells. This permits negatively charged chemical compounds (4) to pass into anodic chamber (30) and thereby be separated from healthy sperm cells in sample output chamber (40).

Advantages of an Integrated Process

The Aitken process described in WO 2005/033295 provides the advantage of being a quick and easy way of enriching sperm cell populations for cells having low incidence of DNA damage and high levels of viability and usefulness in subsequent fertilisation processes.

The process described herein of using electrophoresis to separate chemical compounds from sperm cells similarly provides advantages in terms of a technique that is quick and low on intervention and therefore likely to be do minimal damage to sperm cell function.

Integrating the two processes in accordance with the present invention brings additional advantages including the fact that both processes can be carried out simultaneously thereby reducing the total intervention time (with advantages in terms of reduced risk of loss of sperm cell function) and providing cost savings in terms of a single apparatus only being provided.

Additionally, exposure of sperm cells to chemical agents, whilst carried out in order to provide technical benefits, may in some circumstances carry a potential risk of damaging a portion of sperm cells, for example inducing DNA damage which may make the cells less suitable for subsequent use. Integration with the Aitken process allows sperm cells which may have been damaged by the chemical treatment to be removed from the sample of cells, thereby improving overall sample quality.

Electrical and Other Process Parameters

The strength of the electrical potential and of the current used in the process of the invention and other related parameters may be optimised to the process time, the dimensions of the chambers, the properties of the membranes and the nature of the sperm cells and chemical compounds and electrolytic buffer. Further guidance of selecting appropriate parameters maybe found in the Ainsworth & Aitken papers cited above, which also describe how sperm cell quality before and after separation may be assessed. The conditions may in some circumstances be a combination of all or some of the following:

Buffer may be based on a cell culture medium having an osmolarity to 200 to 400 mOsmol/kg, for example 300 to 320 mOsmol/kg, for example 310 mOsm/kg. A suitable buffer may, for example, comprise 10 mM HEDES, 30 mM sodium chloride and 0.2 M of sugar such as fructose or sucrose. pH is preferably 6 to 9, for example 7 to 8, for example pH7.4.

Conductivity may be from 1 to 10 mS/cm, for example 2 to 5, for example 3.8 to 4.2 mS/cm, for example 4 mS/cm.

Current/voltage applied currents of from 20 to 200 ml mA may be suitable. For example from 50 to 150 mA, for example from 60 to 100 mA, for example from 70 to 80 mA, for example 75 mA. A voltage may be applied between the cathode and anode to give an electrical field strength of 10 to 30 V/cm, for example 15 to 20 V/cm, for example 16 to 18 V/cm, for example 17 V/cm. Voltage may be pulsed with time or modulated into any appropriate waveform in which case the values given immediately above are to be understood as mean values averaged out over the entire electrophoretic time period.

Temperature The temperature is preferably chosen for good sperm survival. For human sperm this might be 15° C. to 40° C., for example 20° C. to 30° C., for example 20° C. to 25° C., for example 23° C.

Time Preferably the process lasts for a few seconds or minutes for example 10 to 1000 seconds. For example 30 to 300, 50 to 500, 10 to 100 seconds.

Membranes

The separation membrane (41) between the sample input chamber and the same output chamber where present should be ion permeable and also permeable to chemical compounds as defined herein and to sperm cells when subject to an electrophoretic force. Preferably it is not permeable to other cell types, for example leukocytes. It may be constructed from any suitable material, for example a plastic material such as polycarbonate, polystyrene, polypropylene or polythene. Polycarbonate may be especially suitable. A pore size of 5 to 50 µm (for example 5 µm or 10 µm) may be especially suitable.

The restriction membranes (21 and 31) between the one or two sample chambers and the respective cathodic and anodic chambers should be ion-permeable and also permeable to chemical compounds but impermeable to sperm cells. It has been found that a membrane having a molecular cut off value of 100 KDa or less, for example 80, 50, 40, 20 or 10 KDa or less is especially suitable. Membranes manufactured by a variety of techniques using various materials may be used. For example a polyacrylamide membrane, optionally provided on a support structure may be suitable.

Construction of Cassette

The cassette (15) may be constructed form any suitable material. Injection moulded plastic (for example, polycarbonate) may be especially suitable due to its ease of production and sterilisation. The chamber arrangements shown in the figures herein are diagrammatic only and other arrangements may be used. Chamber volume may be, for example, between 0.5 µl and 5 ml, or example between 50 µl and 1 ml, for example between 100 µl and 800 µl for example from 200 µl to 600 µl for example approximately 400 µl. The cassette may include input and output means for introduction and withdrawal of material from the chambers.

Subsequent Use Of Sperm Cells

The process of the invention optionally includes the post-separation step of removing the sperm cells from sample output chamber 40, optionally assessing sperm quality (for example using a viability assay such as an eosin exclusion assay, a DNA damage assay such as a TUNEL assay, a mobility assay or simply a cell count), optionally formulating the cells in a suitable medium and then "loading" the cells into a device suitable for insemination, for example intrauterine insemination. Optionally the process further includes the step of carrying out insemination of a female animal or woman, for example by intrauterine insemination. Sperm cells processed in accordance with the first aspect of the invention may be loading into a device suitable for use in IVF or ICSI. Optionally, the process further includes the step of using the sperm cells in an IVF or ICSI procedure.

Accordingly, the invention also provides use of a sperm cell separated from a chemical compound by electrophoresis according to a process of the first aspect of the invention in intrauterine insemination.

Methods of Chemical Pre-Treatment of Sperm Cells

The invention also provides a method of treating sperm cells with a chemical compound in order to increase the sperm cell's fertilisation ability, comprising contacting the sperm cells with a chemical compound and then separating the sperm cells from the chemical compound by electrophoresis comprising subjecting the sperm cells to an electrical potential between a cathode and an anode such that the sperm cells are separated from the chemical compound.

According to this aspect of the invention the sperm-cells, chemical compound may be as described above with reference to other aspects of the invention. The chemical compound is preferably a compound for the promotion of sperm cell motility. The separation process and apparatus may be as described above in reference to the first aspect of the invention. The sperm cells may subsequently be used in intrauterine insemination or prepared for such use.

The invention claimed is:

1. A process for separating sperm cells by electrophoresis from a sperm motility promoting agent to which they have been previously exposed ex vivo, the method comprising:
    subjecting a mixture of the sperm cells and the sperm motility promoting agent to an electric potential between a cathode and an anode, wherein the sperm motility promoting agent is positively charged and electrophoretically mobile,
    wherein the subjecting step simultaneously (1) separates the sperm cells from the sperm motility promoting agent through an ion-permeable membrane, and (2) enriches the sperm cells for sperm cells which carry more sialic acid on their surface and therefore exhibit greater electrophoretic mobility, and
    loading the separated sperm cells into a device suitable for intrauterine insemination,
    wherein the ion-permeable membrane is permeable to the sperm motility promoting agent but not the sperm cells, and wherein the mixture has a pH of 6 to 9.

2. A process according to claim 1, wherein the sperm cells or a portion thereof migrate under the influence of the electrical potential towards the anode.

3. A process as claimed in claim 2, wherein the sperm cells migrate through a sperm cell-permeable membrane which excludes other cell types.

4. A process as claimed in claim 3, wherein the sperm cell-permeable membrane excludes leukocytes.

5. A process as claimed in claim 1, further comprising the steps of:
pre-treating the ex vivo sample of sperm cells with the sperm motility promoting agent for improving sperm cell quality;
placing the ex vivo sample of sperm cells in an ionic solution, in a sample input chamber of an electrophoresis cassette, wherein said sample input chamber is separated from a sample output chamber by a first membrane which is permeable to both ions and sperm cells;
using electrodes to apply an electrical potential across the sample input chamber and sample output chamber such that the sample output chamber is at a more positive electrical potential than the sample input chamber;
allowing the sperm cells or a portion thereof to migrate from the sample input chamber to the sample output chamber;
providing an anodic chamber adjacent to the sample output chamber, said anodic chamber being separated from the sample output chamber by a second membrane comprising an ion permeable membrane which is impermeable to sperm cells such that sperm cells are unable to contact said anode,
wherein the positively charged sperm motility promoting agent migrates under the influence of the electrical potential from the sample input chamber to a cathodic chamber provided adjacent to the sample input chamber and separated from the sample input chamber by a third membrane comprising the ion-permeable membrane thereby achieving separation of the sperm cells from the positively charged sperm motility promoting agent.

6. A process according to claim 5, wherein said first membrane has a pore size of 5 to 50 μm.

7. A process according to claim 1, wherein the electrical potential is applied for less than 5 minutes in order to achieve separation of sperm cells or a portion thereof from the sperm motility promoting agent.

8. A method of treating sperm cells ex vivo with a sperm motility promoting agent, the method comprising
contacting the sperm cells with a sperm motility promoting agent to prepare a mixture, wherein the sperm motility promoting agent is positively charged and electrophoretically mobile, and
separating the sperm cells from the sperm motility promoting agent by electrophoresis, wherein the electrophoresis comprises:
subjecting the mixture to an electrical potential between a cathode and an anode,
wherein the subjecting step simultaneously (1) separates the sperm cells from the sperm motility promoting agent through an ion permeable membrane and (2) enriches the mixture for sperm cells which carry more sialic acid on their surface and therefore exhibit greater electrophoretic mobility, and
loading the separated sperm cells into a device suitable for intrauterine insemination,
wherein the ion-permeable membrane is permeable to the sperm motility promoting agent but not the sperm cells, and wherein the electrophoresis is performed at a pH of 6 to 9.

9. A method of preparing sperm cells for intrauterine insemination, the method comprising:
treating sperm cells with a sperm motility promoting agent, wherein the sperm motility promoting agent is positively charged and electrophoretically mobile,
subjecting a mixture of the sperm cells and the sperm motility promoting agent to electrophoresis by exposing the mixture to an electric potential between a cathode and an anode,
simultaneously (1) separating the sperm cells from the sperm motility promoting agent through an ion-permeable membrane, and (2) enriching the mixture for sperm cells which carry more sialic acid on their surface and therefore exhibit greater electrophoretic mobility, and
loading the separated sperm cells into a device suitable for intrauterine insemination,
wherein the ion-permeable membrane is permeable to the sperm motility promoting agent but not the sperm cells, and wherein the mixture has a pH of 6 to 9.

* * * * *